(12) United States Patent
Wojtasik et al.

(10) Patent No.: US 11,077,155 B2
(45) Date of Patent: Aug. 3, 2021

(54) BACTERIOPHAGE STRAINS AND THEIR APPLICATIONS

(71) Applicant: PROTEON PHARMACEUTICALS S.A., Lodz (PL)

(72) Inventors: Arkadiusz Wojtasik, Lodz (PL); Elzbieta Gorecka, Lodz (PL); Ewelina Wojcik, Lodz (PL); Malgorzata Stanczyk, Lodz (PL); Joanna Kolsut, Lodz (PL); Justyna Klimczak, Lodz (PL); Jaroslaw Dastych, Lodz (PL); Andrzej Siwicki, Lodz (PL); Patrycja Schulz, Lodz (PL)

(73) Assignee: PROTEON PHARMACEUTICALS S.A., Lodz (PL)

( * ) Notice: Subject to any disclaimer, the term of this patent is extended or adjusted under 35 U.S.C. 154(b) by 272 days.

(21) Appl. No.: 16/090,772

(22) PCT Filed: Apr. 3, 2017

(86) PCT No.: PCT/PL2017/050018
§ 371 (c)(1),
(2) Date: Oct. 2, 2018

(87) PCT Pub. No.: WO2017/176136
PCT Pub. Date: Oct. 12, 2017

(65) Prior Publication Data
US 2020/0323931 A1    Oct. 15, 2020

(30) Foreign Application Priority Data
Apr. 3, 2016 (PL) .......................................... 416716

(51) Int. Cl.
A61K 35/76 (2015.01)
C12N 7/00 (2006.01)
A01N 63/40 (2020.01)

(52) U.S. Cl.
CPC .............. *A61K 35/76* (2013.01); *A01N 63/40* (2020.01); *C12N 7/00* (2013.01); *C12N 2795/10121* (2013.01); *C12N 2795/10132* (2013.01); *C12N 2795/10221* (2013.01); *C12N 2795/10233* (2013.01)

(58) Field of Classification Search
CPC .......... A61K 35/76; A01N 63/40; C12N 7/00; C12N 2795/10121; C12N 2795/10132; C12N 2795/10221; C12N 2795/10233; C12N 2795/10232
See application file for complete search history.

(56) References Cited

U.S. PATENT DOCUMENTS

2013/0323209 A1   12/2013   Sung et al.

FOREIGN PATENT DOCUMENTS

WO        2009138752 A2      11/2009
WO        WO-2016170013 A1 *  10/2016   ............. A61K 35/76

OTHER PUBLICATIONS

Verner-Jeffreys DW, Algoet M, Pond MJ, Virdee HK, Bagwell NJ, Roberts EG. Furunculosis in Atlantic salmon (*Salmo salar* L.) is not readily controllable by bacteriophage therapy. Aquaculture. vol. 270, Iss. 1-4, May 18, 2007, pp. 475-484.*
Oliveira, J., Castilho, F., Cunha, A. et al. Bacteriophage therapy as a bacterial control strategy in aquaculture. Aquacult Int 20, 879-910 (2012).*
Silva YJ, Costa L, Pereira C, Mateus C, Cunha A, Calado R, Gomes NC, Pardo MA, Hernandez I, Almeida A. Phage therapy as an approach to prevent Vibrio anguillarum infections in fish larvae production. PLoS One. Dec. 2, 2014;9(12):e114197.*
Richards GP. Bacteriophage remediation of bacterial pathogens in aquaculture: a review of the technology. Bacteriophage. Dec. 20, 2014;4(4):e975540.*
Richards, G.P. "Bacteriophage remediation of bacterial pathogens in aquaculture: a review of the technology", Bacteriophage, 2014; 4(4): e975540, published online Dec. 20, 2014.
Pal, S. "Phage Therapy an alternate disease control in aquaculture: A review on recent advancements" Journal of Agriculture and Veterinary Science, vol. 8, Issue 9 Ver. I (Sep. 2015), pp. 68-81.
Gorski, A. et al. Phage as a Modulator of Immune Responses: Practical Implications for Phage Therapy Advances in Virus Research, vol. 83, 2012, pp. 41-71.

* cited by examiner

*Primary Examiner* — Rachel B Gill
(74) *Attorney, Agent, or Firm* — Arrigo, Lee, Guttman & Mouta-Bellum LLP

(57) ABSTRACT

New strains of bacteriophages and their applications are revealed, useful especially in fish farming.

5 Claims, 4 Drawing Sheets

BACTERIOPHAGE STRAINS AND THEIR APPLICATIONS

The invention relates to novel strains of bacteriophages and their applications useful especially in fish farming.

Aquaculture is the fastest growing sector of the food production worldwide. However, one of the major obstacles preventing effective use of it is the development of infectious diseases among fish which result in vast economic losses estimated in billions of dollars annually. The main etiological factor responsible for development of these infections are bacteria, such as *Aeromonas, Pseudomonas, Vibrio, Yersinia, Edwardsiella, Streptococcus, Lactococus* and *Renibacterium* [Pridgeon J W, 2012, Sudheesh P S, 2012]. As a routine practice, feed are supplemented with antibiotics in treatment of bacterial infections in farmed fish. However, due to the smaller feed intake by sick individuals and impact of different environmental factors, this way of drug administration is not always satisfying. Moreover, intensive application of antibiotics led to appearance of antibiotic resistant bacterial strains that act as reservoir of antibiotic resistance genes. Because of horizontal gene transfer, these genes might be transferred into other pathogens, including human ones, and influence directly human health. Many antimicrobial agents widely used in aquacultures were classified by WHO as having a crucial influence on human health [Almeida A, 2009, Heuer O E, 2009]. Due to the intensive development and importance of fish industry in many regions of the world as well as wide and unregulated application of antibiotics at this field, there is a need of undertaking actions aiming at prevention of antibiotic resistance spread and minimalizing the risk of potential side-effects for human health [Heuer O, 2009]. Application of bacteriophage preparations might be an alternative solution in response to growing antibiotic resistance of bacteria. Bacteriophages are bacterial viruses that occur naturally in the environment and exhibit specificity towards certain bacterial strains or genus [Richards G P, 2014]. In the past, they were used both in treatment and prevention of infectious diseases in humans [Eyer L., 2007]. In recent years, a growing tendency in interest of bacteriophages is observed as well as their use in modern biotechnology as protein and DNA carriers in vaccines and as an alternative for antibiotics [Clark J, 2006]. Results of clinical trials and in vivo studies carried out in the past few years confirm high efficiency and safety of bacteriophage preparations [Pirnay J P, 2012, Eyer J, 2007]. The main advantages of bacteriophage therapy over widely used antibiotics are: specific action only against certain bacterial strains or genus, no acquisition of phage resistance by bacteria thanks to rapid mutation rate of viruses resulting in high activity of bacteriophages against pathogens, relatively low cost of treatment comparing to costs associated with formulations of new antibiotics and lack of side-effects of this therapy [Atterbury R J, 2007, Bhardwaj S B, 2014].

Use of bacteriophage-based vaccines has a lot of advantages: no possession of antibiotic resistance genes, protection of viral DNA against degradation, oral mode of application of such vaccines, relatively inexpensive, easy and very fast production of bacteriophages on a large scale [Clark J, 2006].

There are some data showing the immunomodulatory effect of bacteriophages on the function of both innate cellular and humoral immunity, i.e. phagocytosis, respiratory burst of phagocytes and cytokines production [Gorski A, 2012]. The study of Weber-Dąbrowska et al. has shown the influence of bacteriophages on the control of cytokines production by blood cells [Weber-Dąbrowska B, 2000]. Already published results and patented solutions concentrate mainly on isolation methods and molecular characterization of bacteriophages and to a much lesser extent, on application of phages to treat bacterial pathogens in aquacultures. It was shown that VP-1 phage is specific to *Vibro anguillarum* and *Aeromonas salmonicida* [Pereira C, 2011]. Lytic phages PAS-1 and ASP-1 cause the diminution of *Aeromonas salmonicida* infections in rainbow trout [Kim J H, 2012, Patent Application Publication US 2013/0323209 A1], while phiAS5 phage belonging to Myoviridae family exhibit broad spectrum of activity against Aeromonadaceae and antibiotic resistant *A. salmonicida* subsp. *Salmonicida* strains [Kim J H, 2012]. A protective effect of phages administered orally was confirmed by the studies carried out on fish *Plecoglossus altivelis* infected experimentally with *P. plecoglossicida* [Park S, 2000]. A cocktail consisting of phages PFP1 and PFP12, which were isolated from infected fish, has a strong lytic activity against *Pseudomonas fluorescens* in vitro [Prasad Y, 2010]. A combination of three or more phages causes a lysis of mutants of *A. salmonicida* HER 1107 that are not susceptible to the action of single bacteriophages. It shows the possibility to use bacteriophages in order to protect brown trout against development of furunculosis [Imbeault S, 2006]. A mixture of a few bacteriophages specific to bacteria from *Vibrio* genus may be applied in a treatment of infections caused by *Vibrio* anguillarum in atlantic salmon [Patent Application Publication US 2014/0105866 A]. The use of bacteriophage UP87 in fish *Oreochromis niloticus* reduces the total number of *A. hydrophila* bacteria in blood and does not cause the increase in fish death rate comparing to the results obtained for oxytetracycline [Cruz-Papa D, 2014]. Bacteriophage AH1 totally eliminates mortality in fish infected experimentally with *Aeromonas hydrophila* [Wu J L, 1981]. Application of lytic phage FCP1 in catfish infected experimentally with antibiotic resistant strain of *Flavobacterium columnare* inhibits symptoms of infection and reduces mortality of fish [Prasad Y, 2011].

A remaining problem is such an administration of preparation that would enable the prevention and treatment of fish infected with strains of *Aeromonas* sp. and *Pseudomonas* sp. It is also desirable in order to manufactured preparation would be easy to apply in farming practice, would not cause side-effects and would possess additional health-promoting effects.

Unexpectedly, application of the present invention provides a solution for the problems mentioned above.

The invention relates to bacteriophage for use in prevention and treatment of infections of farm animals, especially fish, caused by pathogenic bacterial strains sensitive to these bacteriophages, wherein said bacteriophage is intended to be given to endangered animals via immersion, favorably at 24-hour time intervals.

Favorably, a treated infection in fish farming is the infection with pathogenic strains of *Aeromonas* sp. and *Pseudomonas* sp., especially the strains of *Aeromonas hydrophila, Aeromonas salmonicida* or *Pseudomonas fluorescens*, wherein used bacteriophage is the bacteriophage strain selected from the group deposited in the Polish Collection of Microorganisms under the following deposition numbers: F/00096 (strain 25AhydR2PP), F/00094 (strain 50AhydR13PP), F/00098 (strain 22PfluR64PP), F/00099 (strain 67PfluR64PP), F/00100 (strain 71PfluR64PP), F/00095 (strain 98PfluR60PP) and F/00101 (strain 60AhydR15PP).

Figure 1:
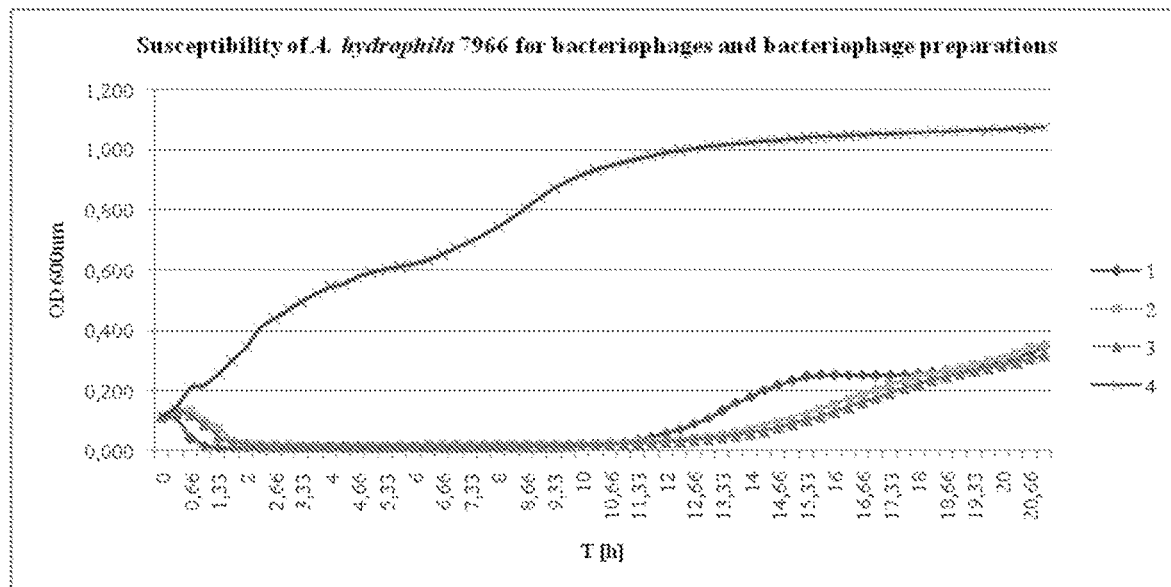

Another aspect of the present invention is a bacteriophage for use in stimulating fish immunity against infections by stimulating both innate and humoral immune systems.

Favorably, used bacteriophage strain is selected from the group deposited in the Polish Collection of Microorganisms under the following deposition numbers: F/00096 (strain 25AhydR2PP), F/00094 (strain 50AhydR13PP), F/00098 (strain 22PfluR64PP), F/00099 (strain 67PfluR64PP), F/00100 (strain 71PfluR64PP), F/00095 (strain 98PfluR60PP) and F/00101 (strain 60AhydR15PP).

The present invention also provides the bacteriophage strain selected from the group deposited in the Polish Collection of Microorganisms under the following deposition numbers: F/00096 (strain 25AhydR2PP), F/00094 (strain 50AhydR13PP), F/00098 (strain 22PfluR64PP), F/00099 (strain 67PfluR64PP), F/00100 (strain 71PfluR64PP), F/00095 (strain 98PfluR60PP) and F/00101 (strain 60AhydR15PP).

DETAILED DESCRIPTION OF THE INVENTION

The present invention provides a method for producing of the bacteriophage preparation used in a prevention and therapy of bacterial infections in fish farming and is characterized by the following steps:

a) a collection of bacteriophage strains specific to selected bacterial strains is built, b) the streaking of selected bacterial strains is performed on solid growth medium which is incubated for 48±3 h at 25° C. (each strain is propagated separately), c) two 96-well plates are prepared: one with liquid growth medium (plate I) and second with solid growth medium (plate II), d) a single bacterial colony is collected from the streaking plate with inoculation loop and transferred to the first well of plate I, shaken vigorously and taken to the solid medium of the first well of plate II with the same inoculation loop; likewise, other pairs of wells are filled, selecting new colonies for each pair and leaving three unfilled wells to control the sterility of the medium, e) plate I is placed in a microplate reader (at 25° C.) and is incubated until the value of optical density $OD_{620}$ reaches 0.2-0.3; afterwards a desired suspension of bacteriophages (for which the production bacterial strain is searched) is added to each well of this plate, it is incubated again in a microplate reader (25° C.) and the value of optical density is recorded until the kinetic curve of bacteriophages multiplication is obtained, based on which bacterial colonies, which are the best hosts for viral multiplication, are selected, f) plate II is incubated for 24±2 h at 25° C. and bacterial colonies which are indicated based on the results from plate I are used to prepare an inoculum of bacterial production strain for given strain of bacteriophage, g) a selected strain of bacterium is cultured from the prepared inoculum in a sterile growth medium, incubated at 25° C. until the suitable optical density is reached ($OD_{620}$) after which a suspension of an appropriate bacteriophage strain is added and incubated for 4 h at 25° C., h) after propagation of bacteriophages, a bacterial biomass is removed from fermentation broth via microfiltration process, obtaining a ready-to-use component of bacteriophage preparation.

Favorably, selected bacterial strains are: *Aeromonas hydrophila* 33658, *Aeromonas hydrophila* 7966, *Aeromonas hydrophila* 49140, *Pseudomonas fluorescens* 4B/UWM/03/13 and *Pseudomonas fluorescens* 8B/UWM/03/13.

The present method is appropriate for fast and easy screening of bacterial colonies that are suitable for very efficient propagation of bacteriophages which is an important feature in industrial applications.

Another aspect of the present invention is the application of a bacteriophage preparation, containing a cocktail of bacteriophages, in a prevention and therapy of bacterial infections in fish farming caused by bacteria from *Aeromonas* and *Pseudomonas* genus. A bacteriophage preparation of the present invention is intended to be given to endangered animals via immersion.

Favorably, the manufactured preparation shows a strong therapeutic effect because it reduces a mortality of fish infected experimentally with *Pseudomonas fluorescens*.

Favorably, a treated infection in fish farming is the infection with pathogenic strains of *Aeromonas hydrophila, Aeromonas salmonicida* and *Pseudomonas fluorescens*. In order to produce the bacteriophage preparation, the appropriate bacteriophage strain is selected from the group deposited in the Polish Collection of Microorganisms 17 Dec. 2015 under the following deposition numbers: F/00096 (strain 25AhydR2PP), F/00094 (strain 50AhydR13PP), F/00098 (strain 22PfluR64PP), F/00099 (strain 67PfluR64PP), F/00100 (strain 71PfluR64PP), F/00095 (strain 98PfluR60PP) and the strain deposited 15 Jan. 2016 under a deposition number F/00101 (strain 60AhydR15PP).

The present invention also provides the bacteriophage strain appropriate for prevention or treatment of infections with pathogenic strains of *Aeromonas hydrophila, Aeromonas salmonicida* and *Pseudomonas fluorescens* selected from the group of; 60AhydR15PP, 25AhydR2PP, 50AhydR13PP, 22PfluR64PP, 67PfluR64PP, 71PfluR64PP and 98PfluR60PP.

The bacteriophage preparation of the present invention is based on natural components of the ecosystem and therefore it does not influence negatively on other organisms than specifically defined pathogenic bacteria. It guarantees that only pathogenic strains of *Aeromonas* sp. and *Pseudomonas* sp. are selectively reduced.

Unexpectedly, the bacteriophage preparation of the present invention is safe and well-tolerated by fish which was confirmed by hematological and biochemical studies on populations of carp and rainbow trout.

Favorably, the bacteriophage preparation of the present invention shows strong immunotropic activity because it influences fish immunity against infections by stimulating both innate and humoral immune systems.

The preparation is intended to use in livestock production especially to fight against pathogenic strains of *Aeromonas hydrophila, Aeromonas salmonicida* and *Pseudomonas fluorescens* in aquaculture.

Bacteriophage strains revealed in this application were identified according to the method of the invention. Unexpectedly, they exhibit a wide range of specificity, being able to lyse at least 4 strains of *P. fluorescens*, 11 strains of *A. hydrophila* and 5 strains of *A. salmonicida*. Bacteriophage strains are stable at cold/refrigeration temperature for at least 3-month storage. Moreover, a propagation of these strains in an industrial scale can be performed successfully without loss of their activity.

In order the invention becomes more evident, it is illustrated on the attached figures.

FIG. 1 presents the results of analysis of susceptibility of *A. hydrophila* 7966 strain for bacteriophages and bacteriophage preparations. 1—*A. hydrophila* 7966 with 25AhydR2PP; 2—*A. hydrophila* 7966 with BAFADOR II; 3—*A. hydrophila* 7966 with BAFADOR III; 4—*A. hydrophila* 7966 with BAFADOR IV; 5—the growth control of *A. hydrophila* 7966.

Figure 2:
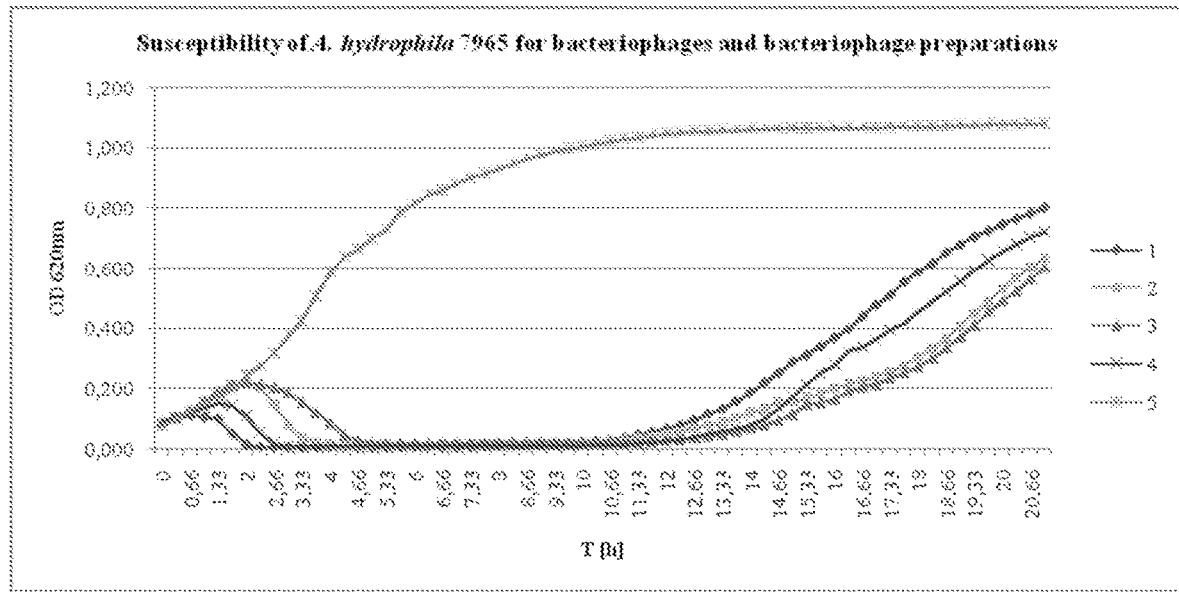

FIG. 2 presents the results of analysis of susceptibility of *A. hydrophila* 7965 strain for bacteriophages and bacteriophage preparations. 1—*A. hydrophila* 7965 with 13AhydR10PP; 2—*A. hydrophila* 7965 with 14AhydR10PP; 3—*A. hydrophila* 7965 with 85AhydR10PP; 4—*A. hydrophila* 7965 with BAFADOR II; 5—the growth control of *A. hydrophila* 7965.

Figure 3:
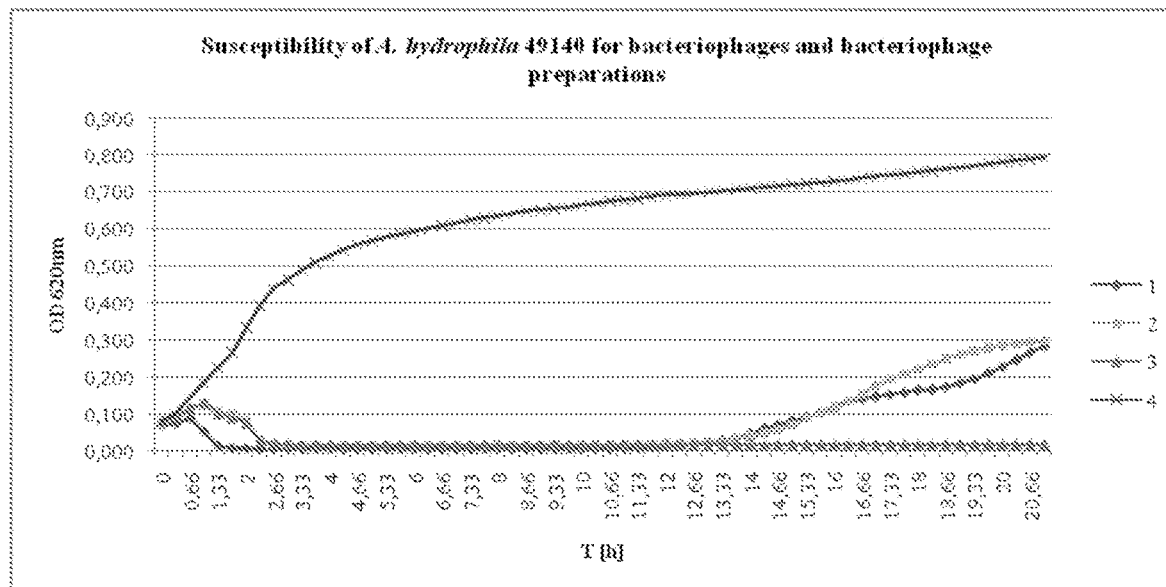

FIG. 3 presents the results of analysis of susceptibility of *A. hydrophila* 49140 strain for bacteriophages and bacteriophage preparations. 1—*A. hydrophila* 49140 with 50AhydR13PP; 2 *A. hydrophila* 49140 with BAFADOR II; 3—*A. hydrophila* 49140 with BAFADOR III; 4—*A. hydrophila* 49140 with BAFADOR IV; 5—the growth control of *A. hydrophila* 49140.

Figure 4:
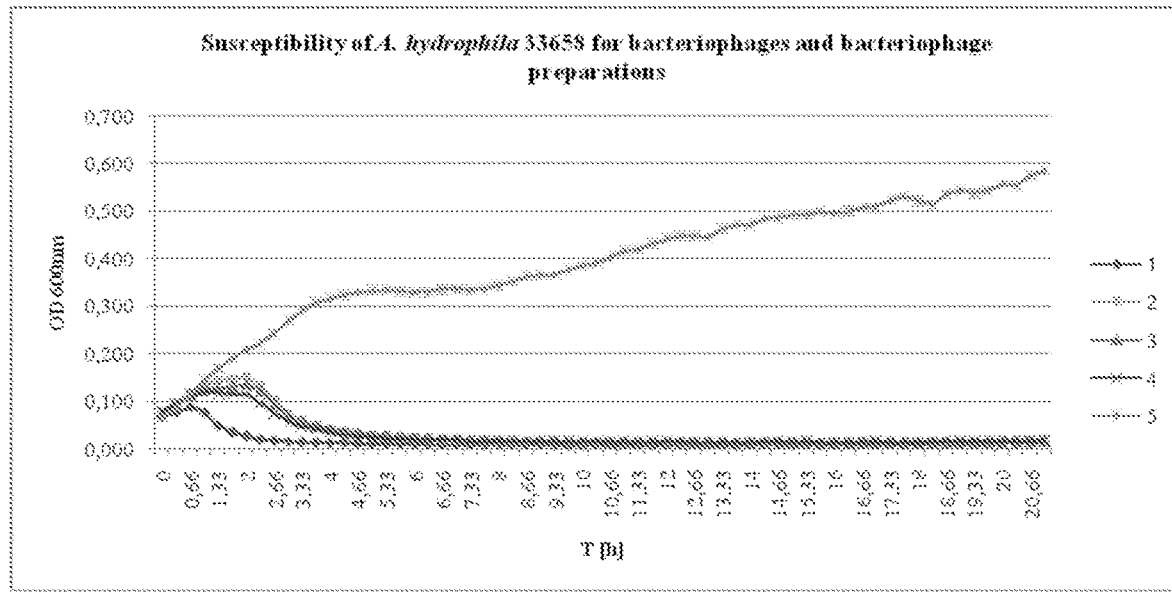

FIG. 4 presents the results of analysis of susceptibility of *A. hydrophila* 33658 strain for bacteriophages and bacteriophage preparations. 1—*A. hydrophila* 33658 with 60AhydR15PP; 2—*A. hydrophila* 33658 with BAFADOR II; 3—*A. hydrophila* 33658 with BAFADOR III; 4—*A. hydrophila* 33658 with BAFADOR IV; 5—the growth control of *A. hydrophila* 33658.

Figure 5:
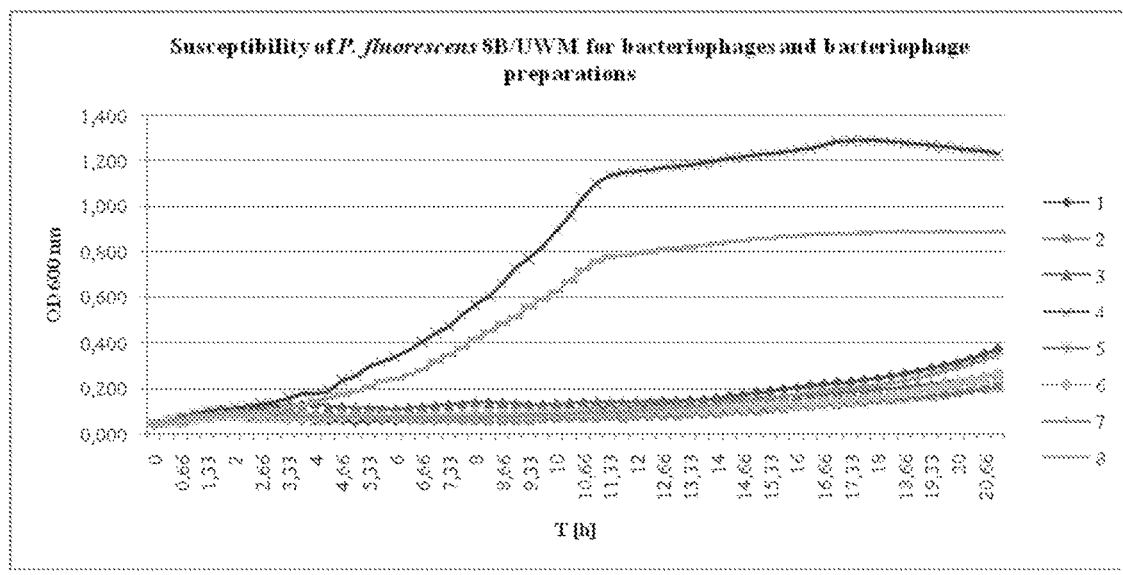

FIG. 5 presents the results of analysis of susceptibility of *P. fluorescens* 8B/UWM strain for bacteriophages and bacteriophage preparations. 1 —*P. fluorescens* 8B/UWM with 22PfluR64PP; 2 —*P. fluorescens* 8B/UWM with 67PfluR64PP; 3 —*P. fluorescens* 8B/UWM with 71PfluR64PP; 4 —*P. fluorescens* 8B/UWM with BAFADOR II; 5 —*P. fluorescens* 8B/UWM with BAFADOR III; 6—*P. fluorescens* 8B/UWM with BAFADOR IV; 7—the growth control of *P. fluorescens* 8B/UWM.

FIGS. 6-9 show restriction profiles of selected bacteriophages.

Figure 6:
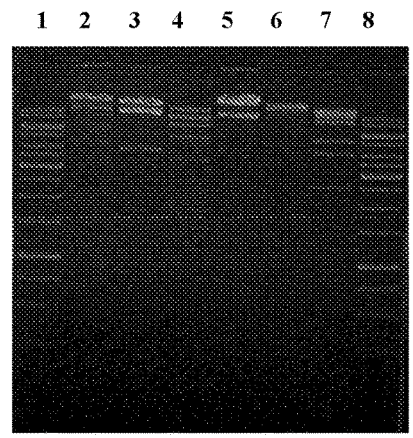

FIG. 6 presents the restriction profile of bacteriophage 60AhydR15PP obtained after digestion with the following restriction enzymes: DraI (lane 2), SspI (lane 4), AseI (lane 6). Lanes 1 and 8—DNA ladder (1 kb).

Figure 7:
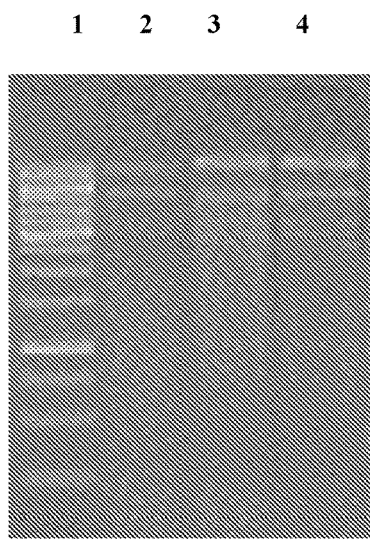

FIG. 7 presents restriction profiles of bacteriophages 22PfluR64PP (lane 2), 67PfluR64PP (lane 3) and 71PfluR64PP (lane 4) obtained after digestion with EcoRI restriction enzyme. Lane 1—DNA ladder (1 kb).

Figure 8:
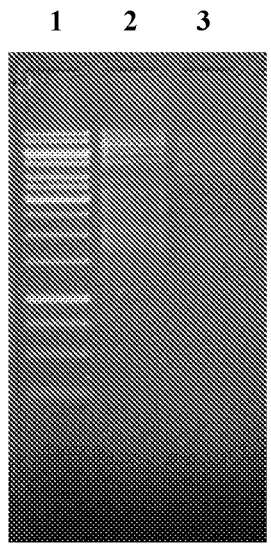

FIG. 8 presents the restriction profile of bacteriophage 50AhydR13PP obtained after the digestion with SspI restriction enzyme (lane 2) and the restriction profile of bacteriophage 98PfluR60PP obtained after the digestion with EcoRI restriction enzyme (lane 3). Lane 1—DNA ladder (1 kb).

Figure 9:
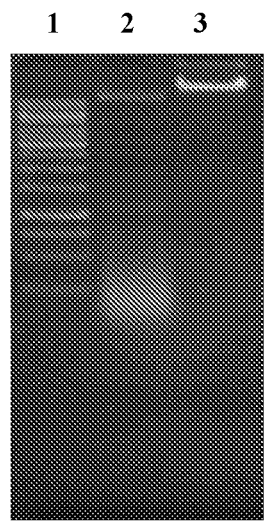

FIG. 9 presents the restriction profile of bacteriophage 25AhydR2PP (lane 2) obtained after the digestion with EcoRI restriction enzyme. Lane 1—DNA ladder (1 kb).

EXAMPLE 1. ISOLATION AND CHARACTERISTIC OF BACTERIOPHAGES

Preparation of Bacterial Strains Collection of the *Aeromonas* Spp. and *Pseudomonas* sp. Genus Isolated from People and Farm Animals.

Initially, the collection of 82 bacterial strains of the *Aeromonas* spp. and *Pseudomonas* sp. was prepared (Table 1). These strains were used to test the specificity of isolated bacteriophages. The collection includes both reference strains available in public repositories and isolates obtained from the Adam Mickiewicz University in Poznan and from the Department of Fish Pathology and Immunology of Inland Fisheries Institute in Olsztyn, and University of Warmia and Mazury in Olsztyn (Table 2).

TABLE 1

Bacterial strain collection of *Aeromonas* sp., *Pseudomonas* sp., *Yersinia* sp., *Renibacterium* sp. and *Enterococcus* sp.

| Code | Strain |
|---|---|
| R1 | *Yersinia ruckeri* 29473 |
| R2 | *Aeromonas hydrophila* 7966 |
| R3 | *Aeromonas hydrophila* 1206101 |
| R4 | *Yersinia ruckeri* 5304100 |
| R5 | *Aeromonas sobria* |
| R6 | *Aeromonas hydrophila* 49140 |
| R7 | *Yersinia ruckeri* 29473 |
| R9 | *Aeromonas hydrophila* 35654 |
| R10 | *Aeromonas hydrophila* 7965 |
| R11 | *Aeromonas hydrophila* 5247167 |
| R12 | *Aeromonas hydrophila* 7965 (290158) |
| R13 | *Aeromonas hydrophila* 49140 |
| R14 | *Aeromonas hydrophila* 33658 (788242) |
| R15 | *Aeromonas hydrophila* 33658 |
| R16 | *Aeromonas hydrophila* 35654 |
| R21 | *Aeromonas hydrophila* RK 70363 |
| R22 | *Aeromonas hydrophila* SK 3 |
| R23 | *Aeromonas hydrophila* ATCC 49140 |
| R24 | *Aeromonas hydrophila* LMG 13656 |
| R25 | *Aeromonas hydrophila* AK 44 |
| R26 | *Aeromonas hydrophila* ATCC 7966$^T$ |
| R27 | *Aeromonas sobria*L MG 13469 |
| R28 | *Aeromonas sobria* CIP 7433$^T$ |
| R29 | *Aeromonas salmonicida* LMG 14900$^T$ |
| R30 | *Aeromonas salmonicida* LMG 3782$^T$ |
| R31 | *Aeromonas salmonicida* CDC 0434-84 |
| R32 | *Aeromonas salmonicida* AK 46 |
| R33 | *Aeromonas salmonicida* LMG 3780$^T$ |
| R34 | *Aeromonas salmonicida*LMG 13450 |
| R40 | 1B/IRS/03/13_*Aeromonas hydrophila* |
| R41 | 2B/IRS/03/13_*Aeromonas hydrophila* |
| R42 | 3B/IRS/03/13_*Aeromonas hydrophila* |
| R43 | 4B/IRS/03/13_*Aeromonas hydrophila* |
| R44 | 5B/IRS/04/13_*Aeromonas hydrophila* |
| R45 | 6B/IRS/05/13_*Aeromonas hydrophila* |
| R46 | 7B/IRS/05/13_*Aeromonas hydrophila* |
| R47 | 8B/IRS/05/13_*Aeromonas hydrophila* |
| R48 | 9B/IRS/05/13_*Aeromonas hydrophila* |
| R49 | 10B/IRS/05/13_*Aeromonas hydrophila* |
| R50 | 11B/IRS/05/13_*Aeromonas hydrophila* |
| R51 | 12B/IRS/06/13_*Aeromonas hydrophila* |
| R52 | 13B/IRS/06/13_*Aeromonas hydrophila* |
| R53 | 1B/IRS/04/14K_*Aeromonas hydrophila* |
| R54 | 2B/IRS/04/14K_*Aeromonas hydrophila* |
| R55 | 3B/IRS/04/14K_*Aeromonas hydrophila* |
| R56 | 4B/IRS/04/14P_*Aeromonas hydrophila* |
| R57 | 1B/UWM/03/13_*Yersinia ruckeri* |
| R58 | 2B/UWM/03/13_*Pseudomonas fluorescens* |
| R59 | 3B/UWM/03/13_*Aeromonas hydrophila* |
| R60 | 4B/UWM/03/13_*Pseudomonas fluorescens* |
| R61 | 5B/UWM/03/13_*Pseudomonas fluorescens* |
| R62 | 6B/UWM/03/13_*Pseudomonas fluorescens* |
| R63 | 7B/UWM/03/13_*Pseudomonas fluorescens* |
| R64 | 8B/UWM/03/13_*Pseudomonas fluorescens* |
| R65 | 9B/UWM/03/13_*Aeromonas hydrophila* |
| R66 | 10B/UWM/03/13_*Yersinia ruckeri* |
| R67 | 11B/UWM/03/13_*Aeromonas hydrophila* |
| R68 | 13B/UWM/03/13_*Pseudomonas fluorescens* |
| R69 | 14B/UWM/03/13_*Yersinia ruckeri* |
| R70 | 15B/UWM/03/13_*Yersinia ruckeri* |
| R71 | 16B/UWM/04/13_*Aeromonas hydrophila/caviae* |
| R72 | 17B/UWM/06/13_*Yersinia ruckeri* |
| R73 | 18B/UWM/06/13_*Aeromonas salmonicida* subsp. *salmonicida* |
| R74 | 19B/UWM/06/13_*Aeromonas salmonicida* subsp. *salmonicida* |
| R75 | 20B/UWM/06/13_*Aeromonas hydrophila* |
| R76 | 21B/UWM/06/13_*Yersinia ruckeri* |
| R77 | 22B/UWM/06/13_*Aeromonas sobria* |
| R78 | 23B/UWM/06/13_*Aeromonas hydrophila* |
| R79 | 24B/UWM/06/13_*Renibacterium salmonicidum* |

TABLE 1-continued

Bacterial strain collection of *Aeromonas* sp., *Pseudomonas* sp., *Yersinia* sp., *Renibacterium* sp. and *Enterococcus* sp.

| Code | Strain |
|---|---|
| R80 | 25B/UWM/07/13__*Aeromonas sobria* |
| R81 | 26B/UWM/07/13__*Aeromonas hydrophila* |
| R82 | 27B/UWM/07/13__*Aeromonas hydrophila* |
| R83 | 28B/UWM/07/13__*Aeromonas sobria* |
| R84 | 29B/UWM/07/13__*Pseudomonas fluorescens* |
| R85 | 30B/UWM/06/14__*Enterococcus* |
| R86 | 1/14P/UWM__*Yersinia ruckeri* |
| R87 | 2/14P/UWM__*Yersinia ruckeri* |
| R88 | 3/14P/UWM__*Yersinia ruckeri* |
| R89 | 31B/UWM/08/14__*Aeromonas hydrophila* |
| R90 | 32B/UWM/08/14__*Aeromonas hydrophila* |
| R91 | 33B/UWM/08/14__*Pseudomonas fluorescens* |
| R92 | 34B/UWM/08/14__*Yersinia ruckeri* |

TABLE 2

Bacterial strains of *Aeromonas* sp., *Pseudomonas* sp., *Yersinia* sp., *Renibacterium* sp. and *Enterococcus* sp.

| No | Bacteria | Number of strains | Source |
|---|---|---|---|
| 1 | *Aeromonas hydrophila* | 6 | UAM |
|   |   | 38 | UWM |
| 2 | *Aeromonas salmonicida* | 6 | UAM |
|   |   | 2 | UWM |
| 3 | *Aeromonas sobria* | 2 | UAM |
|   |   | 4 | UWM |
| 4 | *Pseudomonas fluorescens* | 9 | UWM |
| 5 | *Renibacterium salmonicidum* | 1 | UWM |
| 6 | *Enterococcus* | 1 | UWM |
| 7 | *Yersinia ruckeri* | 13 | UWM |

Isolation of Bacteriophages Active Against Selected Strains of *Aeromonas* Spp. and *Pseudomonas* sp. from Environmental Samples.

Bacteriophages were isolated from samples taken from the intake manifolds, representing an initial stage of the wastewater treatment process, received from the Main Sewage Treatment Plant (GOŚ) in Lodz or from samples of water obtained from the Inland Fisheries Institute (IRS) in Żabieniec (Table 3).

TABLE 3

Isolated bacteriophages and their hosts.

| No | Bacteriophage | Source | Host |
|---|---|---|---|
| 1 | 11AhydR10PP | GOŚ | *Aeromonas hydrophila* 7965 |
| 3 | 13AhydR10PP | GOŚ | *Aeromonas hydrophila* 7965 |
| 4 | 14AhydR10PP | GOŚ | *Aeromonas hydrophila* 7965 |
| 5 | 25AhydR2PP | GOŚ | *Aeromonas hydrophila* 7966 |
| 6 | 50AhydR13PP | GOŚ | *Aeromonas hydrophila* 49140 |
| 7 | 53AhydR13PP | GOŚ | *Aeromonas hydrophila* 49140 |
| 8 | 60AhydR15PP | GOŚ | *Aeromonas hydrophila* 33658 |
| 9 | 62AhydR11PP | GOŚ | *Aeromonas hydrophila* 5247167 |
| 10 | 80AhydR10PP | IRS | *Aeromonas hydrophila* 7965 |
| 11 | 82AhydR10PP | IRS | *Aeromonas hydrophila* 7965 |
| 12 | 85AhydR10PP | IRS | *Aeromonas hydrophila* 7965 |
| 13 | 86AhydR10PP | IRS | *Aeromonas hydrophila* 7965 |
| 14 | 72AsobR5PP | IRS | *Aeromonas sobria* |
| 15 | 75AsobR5PP | IRS | *Aeromonas sobria* |
| 16 | 76AsobR5PP | IRS | *Aeromonas sobria* |
| 17 | 19AhydR15PP | GOŚ | *Aeromonas hydrophila* 33658 |
| 18 | 22PfluR64PP | GOŚ | *Pseudomonas fluorescens* 8B/UWM/03/13 |
| 19 | 23PfluR64PP | GOŚ | *Pseudomonas fluorescens* 8B/UWM/03/13 |
| 20 | 67PfluR64PP | GOŚ | *Pseudomonas fluorescens* 8B/UWM/03/13 |
| 21 | 69PfluR64PP | GOŚ | *Pseudomonas fluorescens* 8B/UWM/03/13 |
| 22 | 70PfluR64PP | GOŚ | *Pseudomonas fluorescens* 8B/UWM/03/13 |
| 23 | 71PfluR64PP | GOŚ | *Pseudomonas fluorescens* 8B/UWM/03/13 |
| 24 | 88PfluR61PP | IRS | *Pseudomonas fluorescens* 5B/UWM/03/13 |
| 25 | 98PfluR60PP | GOŚ | *Pseudomonas fluorescens* 4B/UWM/03/13 |

All bacteriophages used in further experiments were purified by a serial passage to a single plaque on plates with Luria-Bertani (LB) medium. This procedure required at least 5-fold passage.

The specificity of bacteriophages isolated with the plate method was initially determined on the basis of the lytic capacity of phages against selected strains of *Aeromonas* spp., and *Pseudomonas* sp., isolated from diseased fish, obtained from the Department of Fish Pathology and Immunology of Inland Fisheries Institute in Olsztyn (IRS) and the University of Warmia and Mazury in Olsztyn and against selected strains of *Aeromonas* spp., and *Pseudomonas* sp. which constitute the extension of the collection of exemplary strains isolated from patients, obtained from the University of Adam Mickiewicz University in Poznań.

In order to confirm the results, the study of specificity of the isolated phages was repeated 3 times (Tables 4 and 5).

TABLE 4

The specificity of selected bacteriophages against selected model and environmental strains of *Aeromonas* spp. (Proteon Pharmaceuticals bacterial strain collection).

| Bacterial strains | Bacteriophages | | | | | | |
|---|---|---|---|---|---|---|---|
|  | 11AhydR10PP | 13AhydR10PP | 14AhydR10PP | 19AhydR15PP | 25AhydR2PP | 50AhydR13PP | 53AhydR13PP |
| *A. hydrophila* | | | | | | | |
| R2 | − | − | − | − | cl | − | − |
| R6 | − | − | − | − | − | cl | − |
| R9 | − | − | − | − | cl | + | − |
| R10 | − | cl | cl | − | − | − | − |
| R11 | − | − | − | − | − | − | − |
| R12 | − | cl | cl | − | − | − | − |
| R13 | − | − | − | − | − | cl | − |
| R14 | − | cl | − | − | − | cl | − |
| R15 | − | cl | − | − | − | + | − |
| R21 | − | − | − | − | − | cl | − |
| R22 | − | − | − | − | − | cl | − |
| R23 | − | − | − | − | − | cl | − |
| R24 | − | − | − | − | − | cl | − |
| R25 | − | − | − | − | − | cl | − |

TABLE 4-continued

The specificity of selected bacteriophages against selected model and environmental strains of *Aeromonas* spp. (Proteon Pharmaceuticals bacterial strain collection).

| | | | | | | | |
|---|---|---|---|---|---|---|---|
| R26 | – | – | – | – | cl | – | – |
| R40 | cl | – | – | – | – | – | – |
| R41 | – | – | – | – | – | – | cl |
| R48 | – | cl | cl | – | – | – | – |
| R52 | – | cl | cl | – | – | – | – |
| R53 | – | – | – | – | – | – | – |
| R55 | – | – | – | + | – | – | – |
| R59 | – | – | – | – | – | – | – |
| R65 | – | cl | – | – | – | – | – |
| R71 | – | – | – | – | – | – | – |

*A. salmonicida*

| | | | | | | | |
|---|---|---|---|---|---|---|---|
| R30 | – | – | – | – | – | cl | – |
| R31 | – | – | – | – | – | cl | – |
| R32 | – | – | – | – | – | cl | – |
| R33 | – | – | – | – | – | – | – |

*A. sobria*

| | | | | | | | |
|---|---|---|---|---|---|---|---|
| R5 | – | – | – | – | – | – | – |
| R28 | – | – | – | – | – | cl | – |
| R80 | – | – | – | – | – | – | – |

| | Bacteriophages | | | | |
|---|---|---|---|---|---|
| Bacterial strains | 60AhydR15PP | 62AhydR11PP | 80AhydR10PP | 82AhydR10PP | 85AhydR10PP |

*A. hydrophila*

| | | | | | |
|---|---|---|---|---|---|
| R2 | – | – | – | – | – |
| R6 | + | – | – | – | – |
| R9 | + | – | – | – | – |
| R10 | – | – | – | – | – |
| R11 | – | cl | – | – | – |
| R12 | – | – | – | – | cl |
| R13 | cl | – | – | – | – |
| R14 | cl | cl | – | – | – |
| R15 | – | – | – | – | – |
| R21 | – | – | – | – | – |
| R22 | – | – | – | – | – |
| R23 | – | – | – | – | – |
| R24 | cl | cl | – | – | – |
| R25 | cl | cl | – | – | – |
| R26 | – | – | – | – | – |
| R40 | – | – | – | – | – |
| R41 | – | – | – | – | – |
| R48 | – | – | – | cl | cl |
| R52 | – | – | – | cl | cl |
| R53 | – | – | – | + | – |
| R55 | – | – | + | – | – |
| R59 | – | cl | – | – | – |
| R65 | cl | – | – | – | – |
| R71 | – | – | + | – | – |

*A. salmonicida*

| | | | | | |
|---|---|---|---|---|---|
| R30 | cl | cl | – | – | – |
| R31 | cl | cl | – | – | – |
| R32 | – | – | – | – | – |
| R33 | cl | cl | – | – | – |

*A. sobria*

| | | | | | |
|---|---|---|---|---|---|
| R5 | – | cl | – | – | – |
| R28 | – | – | – | – | – |
| R80 | – | – | + | – | – |

| | Bacteriophages | | | |
|---|---|---|---|---|
| Bacterial strains | 86AhydR10PP | 72AsobR5PP | 75AsobR5PP | 76AsobR5PP |

*A. hydrophila*

| | | | | |
|---|---|---|---|---|
| R2 | – | – | – | – |
| R6 | – | – | – | – |
| R9 | – | – | – | – |
| R10 | – | – | – | – |
| R11 | – | – | – | – |

TABLE 4-continued

The specificity of selected bacteriophages against selected model and environmental strains of *Aeromonas* spp. (Proteon Pharmaceuticals bacterial strain collection).

| | | | | |
|---|---|---|---|---|
| R12 | – | – | – | – |
| R13 | – | – | – | – |
| R14 | – | – | – | – |
| R15 | – | – | – | – |
| R21 | – | – | – | – |
| R22 | – | – | – | – |
| R23 | – | – | – | – |
| R24 | – | – | – | – |
| R25 | – | – | – | – |
| R26 | – | – | – | – |
| R40 | – | – | – | – |
| R41 | – | – | – | – |
| R48 | cl | – | – | – |
| R52 | cl | + | – | – |
| R53 | + | – | – | – |
| R55 | – | – | + | – |
| R59 | – | – | – | – |
| R65 | – | – | – | – |
| R71 | – | – | + | – |

*A. salmonicida*

| | | | | |
|---|---|---|---|---|
| R30 | – | – | – | – |
| R31 | – | – | – | – |
| R32 | – | – | – | – |
| R33 | – | – | – | – |

*A. sobria*

| | | | | |
|---|---|---|---|---|
| R5 | – | – | – | – |
| R28 | – | – | – | – |
| R80 | + | + | + | – | cl—total lysis;
+—growth inhibition;
−—no effect

TABLE 5

Specificity of selected bacteriophages against chosen environmental strains of *Pseudomonas* sp. (Proteon Pharmaceuticals bacterial strain collection).

| | Bacteriophages | | | | |
|---|---|---|---|---|---|
| Bacterial strain | 22PfluR64PP | 23PfluR64PP | 67PfluR64PP | 68PfluR64PP | 69PfluR64PP |

*P. fluorescens*

| | | | | | |
|---|---|---|---|---|---|
| R60 | – | – | – | – | – |
| R61 | cl | – | cl | cl | cl |
| R64 | cl | – | cl | cl | – |
| R68 | cl | – | cl | – | – |
| R91 | cl | – | cl | – | – |

| | Bacteriophages | | | |
|---|---|---|---|---|
| Bacterial strain | 70PfluR64PP | 71PfluR64PP | 88PfluR61PP | 98PfluR60PP |

*P. fluorescens*

| | | | | |
|---|---|---|---|---|
| R60 | – | – | – | cl |
| R61 | cl | cl | cl | cl |
| R64 | – | cl | – | – |
| R68 | – | – | – | – |
| R91 | – | cl | – | – | cl—total lysis;
+—growth inhibition;
−—no effect

Isolated bacteriophages were propagated using a host strain as a production strain. These samples were subjected to genomic DNA isolation of bacteriophages based on the modified method of Su et al. [MT Su, 1998].

Genetic Characteristics of Bacteriophages

Isolated DNA of bacteriophages was used to perform restrictive analysis with enzymes: AseI, DraI, SspI and EcoRI. Obtained restriction profiles allowed to define initial genetic characteristic of bacteriophages (FIGS. 6, 7, 8 and 9). Subsequently, after genomes sequencing, more detailed genetic characteristics of bacteriophages was done. Received sequences were analyzed by comparison to genomes of bacteriophages available in BLAST database, then by designation of potential open reading frames in Artemis program and by searching homology to described bacteriophages' proteins using blastp algorithm.

On the basis of performed analysis it was showed that:

Bacteriophage 60AhydR15PP, classified to Myoviridae family (Caudovirales order), contains linear double-stranded DNA (circular form of genome) in size of approximately 165 kbp and shows high similarity to the group of lytic bacteriophages T4, specific against many bacteria from *Aeromonas* sp.

Bacteriophage 25AhydR2PP shows high homology to phage AS7, belonging to T7-like family. It is characterized by linear double-stranded DNA in size of approximately 42 kbp. It belongs to lytic phages.

Bacteriophage 50AhydR13PP shows high homology to phage AS7, belonging to T4-like family. Its genome has size of approximately 165 kbp.

Bacteriophages 22PfluR64PP, 67PfluR64PP, 71PfluR64PP were classified to Podoviridae family (Caudovirales order) with short, unshrinkable tails and icosaedral capsid containing linear double-stranded DNA in size of approximately 40 kbp. They show high similarity to lytic bacteriophages of T7 group specific to many bacteria of the *Pseudomonas* sp.

Sequence of phage 98PfluR60PP did not show similarity to previously known phages families. However, a detailed comparative analysis of particular proteins allowed to find homology with the typical phage proteins necessary to perform a lytic cycle. The genome of 98PfluR60PP is 74 kb in size.

EXAMPLE 2. PREPARATION PRODUCTION

Determination and Optimization of Conditions for the Propagation of Bacteriophages in a Laboratory Scale.

Optimization was carried out for each bacteriophage strain using the host bacterial strain.

The following cultivation conditions were optimized: volume of inoculum of both bacterial and bacteriophage culture, time of cultivation of pure culture and incubation of the infected culture, the cultivation temperature, aeration rate and the type of a growth medium. YES medium at pH 7.0 was selected as the growth medium. The optimum volume of the bacterial inoculum was estimated to be $2 \times 10^9$ CFU per 0.5 liter of the culture medium. Depending on a bacteriophage strain, cultures were adjusted to an optical density $OD_{620}=0.2-0.8$. The optimal growth temperature of the bacterial culture was set to 25° C. Optimized aeration rate for cultivation was reached at 140 rpm in a shaker Ecotron from Infors company. In the process of optimization, it was observed that the addition of 1% by volume of a phage in titer of $10^9$ PFU/ml (5 ml per 0.5 l of culture) was the optimum inoculum of the bacteriophage.

Development of Technology for the Production and Purification of Bacteriophage Suspension.

Stages of Production

1. Amplification in Bioreactor

The first step in the production line is a amplification of the particles of bacteriophages that specifically destroy bacterial cells of selected strains of *Aeromonas* spp., or *Pseudomonas* sp. This is achieved by inoculation of growth medium with the bacterial production strain and cultivation until the appropriate optical density is obtained, then the bacteriophage inoculum is added and the process of proliferation of bacteriophage particles is carried out (conditions discussed above). Once the amplification process is finished, the culture is transferred in a sterile manner using of a peristaltic pump to the next stage of the production process. Each strain of bacteriophages is amplificated as a separate culture. In our research, we used 5-liter (4 liter working volume) airlift bioreactor whose main advantage is the use of modern, disposable amplification bags.

2. Biomass Removal

A completion of the process of amplification of bacteriophages requires the removal of remains of bacteria form a culture broth. For this purpose, the tangential microfiltration is performed using a membrane of a pore size of 0.45 µm, and then microfiltration using a membrane of a pore size of 0.22 µm. This procedure ensures to obtain a sterile suspension with very little decline in titer of phage particles.

3. Assay of the Activity of Manufactured Component

After completion of the filtration process, the phage suspension is subjected to an activity assay expressed as PFU/ml units (plaque forming unit/ml). Determination of the activity is carried out in accordance with the procedure "Enumeration of Bacteriophages in Suspension by Double Agar Overlay Plaque Assay" validated in Proteon Pharmaceuticals SA (Certificate of Good Laboratory Practice No. 10/2015/DPL).

4. Production of the Final Bacteriophage Preparation

In this step, the manufactured components are mixed. Before mixing, the volumes of respective components are calculated, assuring the equal amount of each component in the preparation. Calculations are based on previously determined activity (PFU/ml). The final formulation is then aliquoted and stored at temp. 2-8° C.

EXAMPLE 3. STUDIES OF EFFICIENCY AND SAFETY OF BACTERIOPHAGE PREPARATION

In the conducted studies 3 bacteriophage preparations of the following compositions were used:

BAFADOR II: 60AhydR15PP, 62AhydR11PP, 13AhydR10PP, 14AhydR10PP, 85AhydR10PP, 22PfluR64PP, 67PfluR64PP, 71PfluR64PP, BAFADOR III: 60AhydR15PP, 25AhydR2PP, 50AhydR13PP, 22PfluR64PP, 67PfluR64PP, 71PfluR64PP, 98PfluR60PP BAFADOR IV: 60AhydR15PP, 25AhydR2PP, 50AhydR13PP, 22PfluR64PP, 98PfluR60PP All above preparations were characterized by equivalent amounts of components and activity of $10^8$ PFU/ml.

Bacteriophage preparations were prepared in such a way that each bacteriophage was subjected to the optimized procedure of amplification, removal of bacterial biomass by microfiltration and determination of its activity in PFU/ml. The suspensions of manufactured bacteriophages were mixed in equal amounts obtaining the final bacteriophage preparation. These preparations tested for microbiological purity did not indicate a presence of bacteria.

In Vitro Studies

Based on measurements of optical density ($OD_{620}$) of bacterial strains, the ability of developed bacteriophage preparations and bacteriophage components to reduce the number of bacterial cells was tested.

3 bacteriophage preparations (BAFADOR II, BAFADOR III and BAFADOR IV) and 11 different bacteriophages (13AhydR10PP, 14AhydR10PP, 25AhydR2PP, 50AhydR13PP, 60AhydR15PP, 62AhydR11PP, 85AhydR10PP, 22PfluR64PP, 67PfluR64PP, 71PfluR64PP and 98PfluR60PP) were used in the studies.

5 bacterial strains were used as a test system: *A. hydrophila* 7966, *A. hydrophila* 7965, *A. hydrophila* 49140, *A. hydrophila* 33658 and *P. fluorescens* 8B/UWM.

All experiments were performed in triplicates on 96-well plates. Bacterial cultures of optical density around 0.2 were mixed with suspensions of bacteriophages in 1:1 volume ratio (100 μl:100 μl). Mixtures were incubated at 25° C. for 21 hours. $OD_{620}$ values were recorded every 20 min.

Obtained results are presented on FIGS. 1-5.

Based on obtained results, it was found that mixtures of bacteriophages were much more advantageous in eradication of bacterial strains than individual bacteriophage component. Moreover, these studies confirmed better efficiency of BAFADOR III and BAFADOR IV preparations over BAFADOR II preparation.

In Vivo Studies

The Assessment of Safety of a Prototypical Bacteriophage Preparation in Protection of Farmed Fish Against Bacterial Pathogens.

The studies were carried out in collaboration with the University of Warmia and Mazury.

The Experimental Procedure 1

The experimental material were 20 carps, 20 rainbow trouts and 20 European catfish kept in separate tanks and treated with bacteriophage preparation BAFADOR II at the concentration of $10^5$ PFU/ml for 1 hour via immersion. The assessment of selected hematological and biochemical parameters of fish blood was conducted before administration of bacteriophage preparation BAFADOR II and 1, 2 and 3 days after application.

TABLE 6

The influence of bacteriophage preparation administered via immersion on selected hematological and biochemical parameters in carp (n = 20, mean values ± standard deviation; *statistical significance $p < 0.05$)

| Measured parameters | Days of blood sampling (days after immersion) | | | |
|---|---|---|---|---|
| | Before immersion | 1 | 2 | 3 |
| Erythrocytes count (RBC) (mln/mm) | 1.5 ± 0.4 | 1.6 ± 0.5 | 1.7 ± 0.3 | 1.6 ± 0.3 |
| Hematocrit (Ht) (%) | 32.5 ± 3.2 | 34.5 ± 3.4 | 34.9 ± 3.2 | 33.4 ± 2.9 |
| Hemoglobin (Hb) (g %) | 10.6 ± 1.4 | 11.4 ± 1.4 | 11.6 ± 1.6 | 10.8 ± 1.5 |
| Mean corpuscular hemoglobin (g/L) | 58.4 ± 7.5 | 56.5 ± 8.4 | 55.9 ± 7.5 | 57.9 ± 8.5 |
| Mean corpuscular hemoglobin concentration (g/L) | 25.6 ± 5.5 | 26.4 ± 4.8 | 27.6 ± 5.2 | 26.8 ± 4.9 |
| Cortisol (ng/L) | 179 ± 27 | 185 ± 32 | 191 ± 45 | 187 ± 35 |
| Glucose (mg/L) | 110 ± 15 | 115 ± 14 | 114 ± 12 | 118 ± 16 |
| Aspartate transaminase activity (AST) (U/L) | 84.2 ± 12.5 | 86.5 ± 13.8 | 87.2 ± 14.5 | 88.9 ± 13.3 |
| Alanine transaminase activity (ALT) (U/L) | 2.5 ± 0.8 | 2.7 ± 0.7 | 2.8 ± 0.6 | 2.9 ± 0.8 |

TABLE 7

The influence of bacteriophage preparation administered via immersion on selected hematological and biochemical parameters in rainbow trout (n = 20, mean values ± standard deviation; *statistical significance $p < 0.05$).

| Measured parameters | Days of blood sampling (days after immersion) | | | |
|---|---|---|---|---|
| | Before immersion | 1 | 2 | 3 |
| Erythrocytes count (RBC) (mln/mm) | 2.4 ± 0.5 | 2.8 ± 0.6 | 2.7 ± 0.5 | 2.6 ± 0.4 |
| Hematocrit (Ht) (%) | 39.8 ± 4.5 | 40.5 ± 4.1 | 41.6 ± 3.8 | 42.5 ± 3.9 |
| Hemoglobin (Hb) (g %) | 26.5 ± 3.8 | 28.2 ± 3.2 | 27.8 ± 2.9 | 28.9 ± 3.6 |
| Mean corpuscular hemoglobin (g/L) | 58.4 ± 7.5 | 56.5 ± 8.4 | 55.9 ± 7.5 | 57.9 ± 8.5 |
| Mean corpuscular hemoglobin concentration (g/L) | 31.5 ± 5.2 | 32.8 ± 4.5 | 34.2 ± 4.8 | 33.6 ± 4.2 |
| Cortisol (ng/L) | 192 ± 34 | 198 ± 32 | 197 ± 35 | 191 ± 38 |

TABLE 7-continued

The influence of bacteriophage preparation administered via immersion on selected hematological and biochemical parameters in rainbow trout (n = 20, mean values ± standard deviation; *statistical significance $p < 0.05$).

| Measured parameters | Days of blood sampling (days after immersion) | | | |
|---|---|---|---|---|
| | Before immersion | 1 | 2 | 3 |
| Glucose (mg/L) | 185 ± 23 | 192 ± 26 | 193 ± 27 | 189 ± 25 |
| Aspartate transaminase activity (AST) (U/L) | 96.5 ± 22.4 | 98.5 ± 2.5 | 97.8 ± 24.2 | 98.5 ± 24.4 |
| Alanine transaminase activity (ALT) (U/L) | 4.6 ± 1.2 | 4.9 ± 1.5 | 4.8 ± 1.4 | 4.7 ± 1.7 |

TABLE 8

The influence of bacteriophage preparation administered via immersion on selected hematological and biochemical parameters in catfish (n = 20, mean values ± standard deviation; *statistical significance $p < 0.05$).

| Measured parameters | Days of blood sampling (days after immersion) | | | |
|---|---|---|---|---|
| | Before immersion | 1 | 2 | 3 |
| Erythrocytes count (RBC) (mln/mm) | 1.5 ± 0.5 | 1.7 ± 0.5 | 1.8 ± 0.5 | 1.6 ± 0.5 |
| Hematocrit (Ht) (%) | 19.7 ± 1.5 | 20.8 ± 1.1 | 21.4 ± 1.8 | 20.3 ± 1.9 |
| Hemoglobin (Hb) (g %) | 21.5 ± 2.8 | 22.4 ± 2.2 | 23.8 ± 2.8 | 22.7 ± 2.6 |
| Cortisol (ng/L) | 142 ± 31 | 148 ± 34 | 147 ± 29 | 141 ± 27 |
| Glucose (mg/L) | 165 ± 20 | 162 ± 19 | 163 ± 21 | 168 ± 22 |

Based on the obtained results, it was demonstrated that bacteriophage preparation BAFADOR II had no negative effect on selected hematological parameters (erythrocyte count, hematocrit, hemoglobin), liver enzymes activity: AST, ALT and glucose level up to 3 days after administration in carp (Table 6), rainbow trout (Table 7) and catfish (Table 8). Also, no significant changes in a cortisol level, a hormone secreted during stress, were observed.

The Experimental Procedure 2

The experimental material were 20 carps, 20 rainbow trouts and 20 European catfish kept in separate tanks and treated with bacteriophage preparation BAFADOR II at the concentration of $10^5$ PFU/ml for 1 hour via immersion. The assessment of selected parameters of humoral and cellular immunity in fish blood was conducted before administration of bacteriophage formulation BAFADOR II and 3, 5 and 7 days after application.

TABLE 9

The influence of bacteriophage preparation administered via immersion on selected immune parameters in carp (n = 20, mean values ± standard deviation; *statistical significance $p < 0.05$)

| Measured parameters | Days of blood sampling (days after immersion) | | | |
|---|---|---|---|---|
| | 0 | 3 | 5 | 7 |
| Respiratory burst activity of phagocytes (RBA, OD 620 nm) | 0.46 ± 0.03 | 0.58 ± 0.5* | 0.75 ± 0.05* | 0.85 ± 0.04* |
| Potential killing activity of phagocytes (PKA, OD 620 nm) | 0.38 ± 0.04 | 0.49 ± 0.5* | 0.60 ± 0.04* | 0.75 ± 0.05* |
| Proliferative activity of lymphocytes stimulated by ConA (OD 620 nm) | 0.49 ± 0.05 | 0.62 ± 0.5* | 0.86 ± 0.04* | 0.91 ± 0.05* |
| Proliferative activity of lymphocytes stimulated by LPS (OD 620 nm) | 0.32 ± 0.04 | 0.56 ± 0.7* | 0.69 ± 0.07* | 0.79 ± 0.05* |
| Lysosyme activity in serum (mg/L) | 1.8 ± 0.4 | 2.9 ± 0.6* | 3.6 ± 0.4* | 4.1 ± 0.4* |
| Ceruloplasmin activity in serum (IU) | 64.5 ± 5.9 | 72.5 ± 4.6* | 73.5 ± 4.8* | 74.0 ± 5.2* |
| Total serum protein (g/L) | 43.5 ± 4.0 | 50.3 ± 3.5* | 51.0 ± 4.5* | 50.8 ± 4.2* |
| Ig in serum (g/L) | 7.5 ± 0.6 | 8.9 ± 0.7* | 9.6 ± 0.8* | 10.5 ± 0.7* |

TABLE 10

The influence of bacteriophage preparation administered via immersion on selected immune parameters in rainbow trout (n = 20, mean values ± standard deviation; *statistical significance $p < 0.05$)

| Measured parameters | Days of blood sampling (days after immersion) | | | |
|---|---|---|---|---|
| | 0 | 3 | 5 | 7 |
| Respiratory burst activity of phagocytes (RBA, OD 620 nm) | 0.46 ± 0.03 | 0.58 ± 0.5* | 0.75 ± 0.05* | 0.85 ± 0.04* |
| Potential killing activity of phagocytes (PKA, OD 620 nm) | 0.38 ± 0.04 | 0.49 ± 0.5* | 0.60 ± 0.04* | 0.75 ± 0.05* |
| Proliferative activity of lymphocytes stimulated by ConA (OD 620 nm) | 0.49 ± 0.05 | 0.62 ± 0.5* | 0.86 ± 0.04* | 0.91 ± 0.05* |
| Proliferative activity of lymphocytes stimulated by LPS (OD 620 nm) | 0.32 ± 0.04 | 0.56 ± 0.7* | 0.69 ± 0.07* | 0.79 ± 0.05* |
| Lysosyme activity in serum (mg/L) | 1.8 ± 0.4 | 2.9 ± 0.6* | 3.6 ± 0.4* | 4.1 ± 0.4* |
| Ceruloplasmin activity in serum (IU) | 64.5 ± 5.9 | 72.5 ± 4.6* | 73.5 ± 4.8* | 74.0 ± 5.2* |
| Total serum protein (g/L) | 43.5 ± 4.0 | 50.3 ± 3.5* | 51.0 ± 4.5* | 50.8 ± 4.2* |
| Ig in serum (g/L) | 7.5 ± 0.6 | 8.9 ± 0.7* | 9.6 ± 0.8* | 10.5 ± 0.7* |

TABLE 11

The influence of bacteriophage preparation administered via immersion on selected immune parameters in catfish (n = 20, mean values ± standard deviation; *statistical significance $p < 0.05$)

| Measured parameters | Days of blood sampling (days after immersion) | | | |
|---|---|---|---|---|
| | 0 | 3 | 5 | 7 |
| Respiratory burst activity of phagocytes (RBA, OD 620 nm) | 0.39 ± 0.05 | 0.58 ± 0.4* | 0.72 ± 0.05* | 0.79 ± 0.04* |
| Potential killing activity of phagocytes (PKA, OD 620 nm) | 0.30 ± 0.04 | 0.47 ± 0.4* | 0.58 ± 0.05* | 0.67 ± 0.05* |
| Proliferative activity of lymphocytes stimulated by ConA (OD 620 nm) | 0.41 ± 0.04 | 0.56 ± 0.5* | 0.69 ± 0.06* | 0.75 ± 0.04* |
| Proliferative activity of lymphocytes stimulated by LPS (OD 620 nm) | 0.32 ± 0.04 | 0.47 ± 0.4* | 0.61 ± 0.05* | 0.70 ± 0.05* |
| Lysosyme activity in serum (mg/L) | 2.6 ± 0.4 | 3.4 ± 0.5 | 4.2 ± 0.6* | 4.9 ± 0.5* |
| Ceruloplasmin activity in serum (IU) | 61.0 ± 6.5 | 72.5 ± 4.5* | 74.0 ± 5.5* | 73.0 ± 4.5* |
| Total serum protein (g/L) | 41.5 ± 3.0 | 50.0 ± 3.5 | 51.5 ± 4.0* | 52.0 ± 3.5* |
| Ig in serum (g/L) | 6.8 ± 0.5 | 7.9 ± 0.7 | 8.8 ± 0.5* | 9.5 ± 0.5* |

Based on the obtained results, it was demonstrated that the preparation BAFADOR II caused statistically significant increase in measured parameters of innate cellular immunity (respiratory burst activity and potential killing activity of phagocytes, proliferative activity of lymphocytes) and humoral immunity (lysozyme and ceruloplasmin activity, total serum protein and Ig in serum) in treated fish species. These changes were observed just after 3 days of administration of bacteriophage preparation.

The Assessment of Effectiveness of a Prototypical Bacteriophage Preparation in Protection of Farmed Fish Against Bacterial Pathogens.

The studies were carried out in collaboration with the University of Warmia and Mazury.

Aim of the Study:

The assessment of possibilities of applying bacteriophages to prevent bacterial infections in fish caused by Pseudomonas sp.

The experimental material was carp experimentally infected by intraperitoneal injection of environmental strain

*Pseudomonas fluorescens* isolated from infected fish and identified on biochemical level by API test. Fish were infected with bacterial suspension at a concentration of $6 \times 10^8$ CFU/ml (dose 0.2 ml per fish). Bacteriophage preparations (BAFADOR II, III and IV) were administered via immersion for one hour.

The Experimental Procedure 3

The experimental material were 100 carps randomly divided into 5 equal groups kept in separate tanks. Fish from 2, 3, 4 and 5 groups were experimentally infected by intraperitoneal injection of environmental strain *Pseudomonas fluorescens* isolated from infected fish and identified using the API test. Fish were infected with bacterial suspension at a concentration of $6 \times 10^8$ CFU/ml (dose 0.2 ml per fish). Bacteriophage preparation (BAFADOR II) was administered via immersion at a concentration of $10^5$ PFU/ml for one hour.

TABLE 12

Scheme of application of bacteria and bacteriophages.

| No | Number of fish | Description of experiment |
|---|---|---|
| 1 | 20 | Negative control not infected and not treated with bacteriophage preparation |
| 2 | 20 | Positive control infected with *P. fluorescens* at a concentration of $6 \times 10^8$ CFU/ml (dose 0.2 ml/fish) |
| 3 | 20 | Group infected with *P. fluorescens*: at a concentration of $6 \times 10^8$ CFU/ml (dose 0.2 ml/fish) and treated with bacteriophage preparation (BAFADOR II) at a concentration of $10^5$ PFU/ml (25 ml of preparation in concentration of $10^8$ PFU/ml per 2.5 L of water, 1 h bath) 24 h after infection |
| 4 | 20 | Group infected with *P. fluorescens*: at a concentration of $6 \times 10^8$ CFU/ml (dose 0.2 ml/fish) and treated with bacteriophage preparation (BAFADOR II) at a concentration of $10^5$ PFU/ml (25 ml of preparation in concentration of $10^8$ PFU/ml per 2.5 L of water, 1 h bath) 48 h after infection |
| 5 | 20 | Group infected with *P. fluorescens*: at a concentration of $6 \times 10^8$ CFU/ml (dose 0.2 ml/fish) and treated with bacteriophage preparation (BAFADOR II) at a concentration of $10^5$ PFU/ml (25 ml of preparation in concentration of $10^8$ PFU/ml per 2.5 L of water, 1 h bath) 24 h and 48 h after infection |

Mortality rate of fish was estimated during the experiment (Table 13). Based on obtained results, it was demonstrated that bacteriophage preparation caused decrease in a death rate of fish in groups treated with bacteriophages both after 24 (group 3), and 48 hours (group 4) after experimental infection with *Pseudomonas fluorescens* (20 and 30% of deaths, respectively). The strongest therapeutic effect was observed after double administration of preparation by immersion 24 and 48 hours after infections (group 5; 15% of deaths).

TABLE 13

The mortality of farmed carp after experimental infection with *P. fluorescens* and administration of bacteriophage preparation (BAFADOR II).

| Date | No of group | | | | |
|---|---|---|---|---|---|
| | 1 | 2 | 3 | 4 | 5 |
| 2 Oct. 2015 | 0 | 0 | 0 | 0 | 0 |
| 3 Oct. 2015 | 0 | 1 | 0 | 0 | 0 |
| 4 Oct. 2015 | 0 | 3 | 1 | 2 | 0 |
| 5 Oct. 2015 | 0 | 3 | 1 | 2 | 1 |
| 6 Oct. 2015 | 0 | 3 | 1 | 1 | 1 |
| 7 Oct. 2015 | 0 | 1 | 1 | 1 | 1 |
| 8 Oct. 2015 | 0 | 0 | 0 | 0 | 0 |
| Mortality (in pieces) | 0 | 11 | 4 | 6 | 3 |
| Total mortality | 0% | 55% | 20% | 30% | 15% |

The Experimental Procedure 4

The experimental material were 100 carps randomly divided into 5 equal groups kept in separate tanks. Fish from 2, 3, 4 and 5 groups were experimentally infected by intraperitoneal injection of environmental strain *Pseudomonas fluorescens* isolated from infected fish and identified using the API test. Fish were infected with bacterial suspension at a concentration of $6 \times 10^8$ CFU/ml (dose 0.2 ml per fish). Bacteriophage preparation (BAFADOR III) was administered by immersion at a concentration of $10^5$ PFU/ml for one hour.

TABLE 14

Scheme of application of bacteria and bacteriophages

| No | Number of fish | Description of experiment |
|---|---|---|
| 1 | 20 | Negative control not infected and not treated with bacteriophage preparation |
| 2 | 20 | Positive control infected with *P. fluorescens* at a concentration of $6 \times 10^8$ CFU/ml (dose 0.2 ml/fish) |
| 3 | 20 | Group infected with *P. fluorescens* at a concentration of $6 \times 10^8$ CFU/ml (dose 0.2 ml/fish) and treated with bacteriophage preparation (BAFADOR III) at a concentration of $10^5$ PFU/ml (25 ml of preparation at a concentration of $10^8$ PFU/ml per 2.5 L of water, 1 h bath) 24 h after infection |
| 4 | 20 | Group infected with *P. fluorescens* at a concentration of $6 \times 10^8$ CFU/ml (dose 0.2 ml/fish) and treated with bacteriophage preparation (BAFADOR III) at a concentration of $10^5$ PFU/ml (25 ml of preparation in concentration of $10^8$ PFU/ml per 2.5 L of water, 1 h bath) 48 h after infection |
| 5 | 20 | Group infected with *P. fluorescens* at a concentration of $6 \times 10^8$ CFU/ml (dose 0.2 ml/fish) and treated with bacteriophage preparation (BAFADOR III) at a concentration of $10^5$ PFU/ml (25 ml of preparation at a concentration of $10^8$ PFU/ml per 2.5 L of water, 1 h bath) 24 h and 48 h after infection |

Mortality rate of fish was estimated during the experiment (Table 15). Obtained results show that bacteriophage preparation of the present invention reduced mortality of fish in groups treated with bacteriophages, both after 24 (group 3), and 48 hours (group 4) after experimental infection with *Pseudomonas fluorescens* (15 and 25% of deaths, respectively). The strongest therapeutic effect was observed after double administration of preparation by immersion 24 and 48 hours after infections (group 5; 10% of deaths).

TABLE 15

Mortality rate of carp culture after experimental
infection with P. fluorescens and treatment
with bacteriophage preparation (BAFADOR III).

| Date | No of group | | | | |
|---|---|---|---|---|---|
| | 1 | 2 | 3 | 4 | 5 |
| 12 Oct. 2015 | 0 | 0 | 0 | 0 | 0 |
| 13 Oct. 2015 | 0 | 1 | 0 | 0 | 0 |
| 14 Oct. 2015 | 0 | 3 | 1 | 1 | 0 |
| 15 Oct. 2015 | 0 | 3 | 1 | 2 | 1 |
| 16 Oct. 2015 | 0 | 3 | 1 | 1 | 1 |
| 17 Oct. 2015 | 0 | 0 | 0 | 1 | 0 |
| 18 Oct. 2015 | 0 | 0 | 0 | 0 | 0 |
| Mortality (in pieces) | 0 | 10 | 3 | 5 | 2 |
| Total mortality | 0% | 50% | 15% | 25% | 10% |

The Experimental Procedure 5

The experimental material were 100 carps randomly divided into 5 equal groups kept in separate tanks. Fish from 2, 3, 4 and 5 groups were experimentally infected by intraperitoneal injection of environmental strain *Pseudomonas fluorescens* isolated from infected fish and identified using biochemical test API. Fish were infected with bacterial suspension at a concentration of $6 \times 10^8$ CFU/ml (dose 0.2 ml per fish). Bacteriophage preparation (BAFADOR IV) was administered via immersion at a concentration of $10^5$ PFU/ml for one hour.

TABLE 16

Scheme of application of bacteria and bacteriophages

| No | Number of fish | Description of experiment |
|---|---|---|
| 1 | 20 | Negative control not infected and not treated with bacteriophage preparation |
| 2 | 20 | Positive control infected with P. fluorescens at a concentration of $6 \times 10^8$ CFU/ml (dose 0.2 ml/fish) |
| 3 | 20 | Group infected with P. fluorescens at a concentration of $6 \times 10^8$ CFU/ml (dose 0.2 ml/fish) and treated with bacteriophage preparation (BAFADOR IV) at a concentration of $10^5$ PFU/ml (25 ml of preparation in concentration of $10^8$ PFU/ml per 2.5 L of water, 1 h bath) 24 h after infection |
| 4 | 20 | Group infected with P. fluorescens at a concentration of $6 \times 10^8$ CFU/ml (dose 0.2 ml/fish) and treated with bacteriophage preparation (BAFADOR IV) at a concentration of $10^5$ PFU/ml (25 ml of preparation in concentration of $10^8$ PFU/ml per 2.5 L of water, 1 h bath) 48 h after infection |
| 5 | 20 | Group infected with P. fluorescens at a concentration of $6 \times 10^8$ CFU/ml (dose 0.2 ml/fish) and treated with bacteriophage preparation (BAFADOR IV) at a concentration of $10^5$ PFU/ml (25 ml of preparation in concentration of $10^8$ PFU/ml per 2.5 L of water, 1 h bath) 24 h and 48 h after infection |

Mortality rate of fish was estimated during the experiment (Table 17). Obtained results show that bacteriophage preparation of the present invention reduced mortality of fish in groups treated with bacteriophages, both after 24 (group 3), and 48 hours (group 4) after experimental infection with *Pseudomonas fluorescens* (15 and 25% of deaths, respectively). The strongest therapeutic effect was observed after double administration of preparation by immersion 24 and 48 hours after infection (group 5; 10% of deaths).

TABLE 17

The mortality of farmed carp after experimental
infection with P. fluorescens and treatment
with bacteriophage preparation (BAFADOR IV).

| Date | No of group | | | | |
|---|---|---|---|---|---|
| | 1 | 2 | 3 | 4 | 5 |
| 22 Oct. 2015 | 0 | 0 | 0 | 0 | 0 |
| 23 Oct. 2015 | 0 | 1 | 0 | 0 | 0 |
| 24 Oct. 2015 | 0 | 3 | 1 | 1 | 0 |
| 25 Oct. 2015 | 0 | 3 | 1 | 2 | 1 |
| 26 Oct. 2015 | 0 | 2 | 1 | 1 | 0 |
| 27 Oct. 2015 | 0 | 1 | 0 | 1 | 1 |
| 28 Oct. 2015 | 0 | 0 | 0 | 0 | 0 |
| Mortality (in pieces) | 0 | 11 | 3 | 5 | 2 |
| Total mortality | 0% | 55% | 15% | 25% | 10% |

Based on conducted experiments, it was demonstrated that a death rate of fish was significantly reduced in groups treated with bacteriophages, both in 24 and 48 hours after experimental infection with *Pseudomonas fluorescens*. The strongest therapeutic effect was observed after double administration of preparation by immersion 24 and 48 hours after infection. Moreover, it was observed that fish mortality was the smallest in the experiments in which bacteriophage preparations BAFADOR III and BAFADOR IV were applied. In these studies, a death rate after double administration of preparations was at the level of 10% while in case of BAFADOR II at the level of 15%.

Summary of results concerning safety and efficiency of bacteriophage preparations in farmed fish.
1. Bacteriophage preparation does not affect biochemical and hematological blood parameters in farmed fish.
2. Bacteriophage preparation stimulates both innate cellular and humoral immune systems in farmed fish.
3. Bacteriophage preparation reduces mortality of farmed fish infected with a pathogenic bacterial strain.

REFERENCES

Pridgeon J W, and Klesius P K. Major bacterial diseases in aquaculture and their vaccine development. CAB Reviews 2012, 7, No. 048doi: 10.1079/PAVSNNR20127048.

Sudheesh P S, Al-Ghabshi A, Al-Mazrooei N, Al-Habsi S. Comparative pathogenomics of bacteria causing infectious diseases in fish. Int J Evol Biol. 2012; 2012:457264.

Almeida A, Cunha A, Gomes N C, Alves E, Costa L, Faustino M A. Phage therapy and photodynamic therapy: low environmental impact approaches to inactivate microorganisms in fish farming plants. Mar Drugs. 2009, 30; 7(3):268-313.

Heuer O E, Kruse H, Grave K, Collignon P, Karunasagar I, Angulo F J. Human health consequences of use of antimicrobial agents in aquaculture. Clin Infect Dis. 2009, 15; 49(8):1248-53.

Richards G P. Bacteriophage remediation of bacterial pathogens in aquaculture: a review of the technology, Bacteriophage, 4:4, e975540, DOI: 10.4161/21597081.2014.97554.

Eyer L, Pantůcek R, Růzicková V, Doskar J. [New perspectives of the phage therapy]. Klin Mikrobiol Infekc Lek. 2007, 13(6):231-5

Clark J R, March J B. Bacteriophages and biotechnology: vaccines, gene therapy and antibacterials. Trends Biotechnol. 2006, 24(5):212-8.

Pirnay J P, Verbeken G, Rose T, Serge Jennes S, Zizi M, Isabelle Huys I, Rob Lavigne R, Maia Merabishvili M, Mario Vaneechoutte M, Angus Buckling A, De Vos D. Introducing yesterday's phage therapy in today's medicine. Future Virol. 2012, 7(4): 379-390.

Atterbury R J, Van Bergen M A, Ortiz F, Lovell M A, Harris J A, De Boer A, Wagenaar J A, Allen V M, Barrow P A. Bacteriophage therapy to reduce salmonella colonization of broiler chickens. Appl Environ Microbiol. 2007, 73(14):4543-9.

Bhardwaj S B. Bacteriophage Therapy: A possible new alternative for oral diseases. Int. J. Curr. Microbiol. App. Sci. 2014, 3(6) 437-442.

Górski A, Międzybrodzki R, Borysowski J, Dąbrowska K, Wierzbicki P, Ohams M, Korczak-Kowalska G, Olszowska-Zaremba N, usiak-Szelachowska M, Klak M, Jończyk E, Kaniuga E, Goaś A, Purchla S, Weber-Dąbrowska B, Letkiewicz S, Fortuna W, Szufnarowski K, Paweczyk Z, Rogóż P, Kosowska D. Phage as a modulator of immune responses: practical implications for phage therapy. Adv Virus Res. 2012, 3:41-71.

Weber-Dąbrowska B, Mulczyk M, Górski A. Bacteriophage therapy of bacterial infections: an update of our institute's experience. Arch Immunol Ther Exp (Warsz). 2000, 48(6):547-51.

Pereira C, Silva Y J, Santos A L, Cunha A, Gomes N C, Almeida A. Bacteriophages with potential for inactivation of fish pathogenic bacteria: survival, host specificity and effect on bacterial community structure. Mar Drugs. 2011, 9(11):2236-55.

Kim J H, Son J S, Choi Y J, Choresca C H, Shin S P, Han J E, Jun J W, Kang D H, Oh C, Heo S J, Park S C. Isolation and characterization of a lytic Myoviridae bacteriophage PAS-1 with broad infectivity in Aeromonas salmonicida. CurrMicrobiol. 2012, 64(5):418-26.

United States Patent Application Publication US 2013/0323209 A1. Novel bacteriophage and its use for preventing proliferation of pathogenic bacteria.

Kim J H, Son J S, Choi Y J, Choresca C H, Shin S P, Han J E, Jun J W, Park S C. Complete genomic sequence of a T4-like bacteriophage, phiAS4, infecting Aeromonas salmonicida subsp. salmonicida. Arch Virol. 2012, 157(2): 391-5.

Park S C, Shimamura I, Fukunaga M, Mori K I, Nakai T. Isolation of bacteriophages specific to a fish pathogen, Pseudomonas plecoglossicida, as a candidate for disease control. Appl Environ Microbiol. 2000, 66(4):1416-22.

Prasad Y, Kumar D, Sharma A K, Nisha D, Ninawe A S. Isolation and efficacy characterizations of lytic bacteriophages against antibiotic resistant Pseudomonas fluorescens from Sub Himalaya region. Biochem. Cell. Arch. 2010, 10:21-29.

Imbeault S, Parent S, Lagace M, Uhland C F, Blais J F. Using Bacteriophages to prevent furunculosis caused by Aeromonas salmonicida in farmed brook trout. J Aquat Anim Health 2006, 18 (3): 203-214.

United States Patent Application Publication US 2014/0105866 A1. Bacteriophages useful for the prophylaxis and therapy of Vibrio anguillarum.

Cruz-Papa D, Candare C M, Cometa G L, Gudez D E, Guevara A M, Relova M B, Pap R D. Aeromonas hydrophila Bacteriophage UP87: An Alternative to Antibiotic Treatment for Motile Aeromonas Septicemia in Nile Tilapia (Oreochromisniloticus). The Philippine agriculturist 2014, 97(1):96-101.

Wu J L, Hui-Ming Lin H M, Jan L, Hsu Y L, Chang L H. Biological Control of Fish Bacterial Pathogen, Aeromonas hydrophila, by Bacteriophage AH 1. Fish Pathology 1981, 15 (3/4):271-276.

Prasad Y, Arpana, Kumar D, Sharma A K. Lytic bacteriophages specific to Flavobacterium columnare rescue catfish, Clariasbatrachus (Linn.) from columnaris disease. J Environ Biol. 2011, 32(2):161-8.

Su M T, Tyamagondlu V. V., Bodmer R. 1998. Large- and small-scale preparation of bacteriophage lambda lysate and DNA. BioTechniques, 25(1): 44-6.

The invention claimed is:

1. A method of preventing or treating an infection in a farmed fish, comprising treating the farmed fish by immersion in a composition comprising at least $10^5$ PFU/ml of bacteriophage, wherein the bacteriophage is selected from the group consisting of: strain 25AhydR2PP (deposited in the Polish Collection of Microorganisms under accession number F/00096), strain 50AhydR13PP (deposited in the Polish Collection of Microorganisms under accession number F/00094), strain 22PfluR64PP (deposited in the Polish Collection of Microorganisms under accession number F/00098), strain 67PfluR64PP (deposited in the Polish Collection of Microorganisms under accession number F/00099), strain 71PfluR64PP (deposited in the Polish Collection of Microorganisms under accession number F/00100), strain 98PfluR60PP (deposited in the Polish Collection of Microorganisms under accession number F/00095), and strain 60AhydR15PP (deposited in the Polish Collection of Microorganisms under accession number F/00101).

2. The method of claim 1, wherein the treatment is for a period comprising one hour.

3. The method of claim 1, wherein the treatment is repeated at 24-hour time intervals.

4. The method of claim 1, wherein the infection is an infection of an Aeromonas sp. or a Pseudomonas sp.

5. The method of claim 4, wherein the infection is an infection by Aeromonas hydrophila, Aeromonas salmonicida or Pseudomonas fluorescens.

* * * * *